United States Patent
Tobias

(10) Patent No.: US 7,937,984 B2
(45) Date of Patent: *May 10, 2011

(54) GAS SENSOR TEST SYSTEM AND METHODS RELATED THERETO

(75) Inventor: Peter Tobias, Minnetonka, MN (US)

(73) Assignee: Honeywell International Inc., Morristown, NJ (US)

( * ) Notice: Subject to any disclaimer, the term of this patent is extended or adjusted under 35 U.S.C. 154(b) by 589 days.

This patent is subject to a terminal disclaimer.

(21) Appl. No.: 11/618,404

(22) Filed: Dec. 29, 2006

(65) Prior Publication Data

US 2008/0156074 A1     Jul. 3, 2008

(51) Int. Cl.
*G01N 27/00* (2006.01)
*G01N 33/22* (2006.01)

(52) U.S. Cl. .......................... 73/1.06; 73/23.2

(58) Field of Classification Search ........... 73/1.01–1.07
See application file for complete search history.

(56) References Cited

U.S. PATENT DOCUMENTS

| | | | |
|---|---|---|---|
| 4,387,165 A * | 6/1983 | Youngblood | 436/121 |
| 4,654,624 A * | 3/1987 | Hagan et al. | 338/34 |
| 4,825,683 A * | 5/1989 | Takami et al. | 73/1.06 |
| 5,535,614 A * | 7/1996 | Okamoto et al. | 73/23.31 |
| 6,632,674 B1 | 10/2003 | Warburton | |
| 2004/0227087 A1* | 11/2004 | Markham et al. | 250/339.08 |
| 2005/0155405 A1* | 7/2005 | Sasaki et al. | 73/1.06 |
| 2005/0262924 A1 | 12/2005 | Wood et al. | |
| 2006/0042351 A1 | 3/2006 | Liu et al. | |
| 2006/0230813 A1* | 10/2006 | Tschuncky et al. | 73/23.2 |

FOREIGN PATENT DOCUMENTS

| | | |
|---|---|---|
| GB | 1285954 | 8/1972 |
| JP | 1099801 | 4/2001 |
| WO | WO-00/60346 | 10/2000 |

OTHER PUBLICATIONS

K. Brudzewski, "An attempt to apply Elman's neural-network to the recognition of methane pulses." Sensors and Actuators B. 47. (1998) pp. 231-234.*
B-U. Moon, J-M. Lee, G-H Shim, M-B Lee, J-H Lee, D-D Lee, J-H Lee, "Silicon bridge type micro-gas sensor array." Sensors and Actuators B. 108. (Feb. 20, 2005) pp. 271-277.*
M. Penza, G. Cassano, F. Tortorella, "Gas recognition by activated WO3 thin film sensors array." Sensors and Actuators B 81 (2001) 115-121.*
M. Krawczyk and J. Namiesnik. "Application of a catalytic combustion sensor (Pellistor) for the monitoring of the explosiveness of a hydrogen-air mixture in the upper explosive limit range." Journal of Automated Methods & Management in Chemistry. vol. 25, No. 5 (Sep.-Oct. 2003) pp. 115-122.*
"JP 2001-099801—JPO English Machine Translation".
"JP 2001-099801 Derwent Abstract".

* cited by examiner

*Primary Examiner* — Lisa M Caputo
*Assistant Examiner* — Punam Roy
(74) *Attorney, Agent, or Firm* — Schwegman, Lundberg & Woessner P.A.

(57) ABSTRACT

Embodiments of the present invention relate a gas sensor system comprising a gas generating device adapted to generate a test gas, a target gas sensor positioned near the gas generating device, a test gas sensor positioned near the gas generating device and in communication with the target gas sensor and wherein the test gas sensor is sensitive to the test gas.

9 Claims, 1 Drawing Sheet

GAS SENSOR TEST SYSTEM AND METHODS RELATED THERETO

FIELD OF THE INVENTION

Embodiments of the present invention relate to a gas sensor test system. More specifically, embodiments of the present invention relate to the utilization of a second, selective and stable sensor for the testing of a first sensor.

BACKGROUND

The reliability of toxic gas detectors is of great importance in many applications, especially when these instruments are used for ensuring the safety of personnel. Reliability is typically obtained by periodic checking of the instrument response to a test gas, however calibration test gases are typically supplied in large, bulky and expensive gas cylinders.

Potentially hazardous atmospheres are found in many locations, due to the presence of toxic gases, combustible gas mixtures or the excess or deficiency of oxygen concentration. Many types of gas detection instruments have been developed to provide a warning that the atmosphere contains potentially hazardous components, or to initiate remedial action. Examples of these gas detection instruments include the detection of combustible gases in coal mines, hydrogen sulfide in oil fields and water treatment plants, carbon monoxide in places ranging from steel mills to bedrooms, and oxygen in confined spaces, such as sewers. Within each gas detection instrument there are one or more gas sensors, whose function is to provide an electrical signal, which varies in response to the gas concentration.

Most gas sensors provide a relative output signal, such that the output signal is not an absolute measure of gas concentration, but merely proportional to the gas concentration. In such cases, the gas sensor must be calibrated with a known test gas prior to use. Calibration can also be used as a function check to ensure the sensor is working. The output from many types of sensors can vary over time and sensors can fail to operate without warning. Frequently calibrating a gas sensor can be time consuming, expensive and cumbersome in many applications. Calibrating a gas sensor is also limited to the reproducibility of the amount of test gas in contact with the sensor.

SUMMARY

Embodiments of the present invention relate a gas sensor system comprising a gas generating device adapted to generate a test gas, a target gas sensor positioned near the gas generating device, a test gas sensor positioned near the gas generating device and in communication with the target gas sensor and wherein the test gas sensor is sensitive to the test gas.

Embodiments of the present invention also relate to a method for testing a gas sensor. The method comprises generating a test gas, contacting a test sensor with test gas sufficient to determine an amount of test gas in contact and contacting a target sensor with test gas sufficient to test target sensor.

DETAILED DESCRIPTION

References in the specification to "one embodiment," "an embodiment," "an example embodiment," indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Embodiments of the present invention relate to a gas sensor test system. By utilizing a second, stable sensor, a gas sensor test system may be able to more accurately determine the amount of test gas introduced to a target sensor for testing. The second sensor may be inexpensive and not sensitive to the target gas or have low baseline drift. The second sensor, or test sensor, may be utilized to determine the actual concentration of test gas in contact with a target sensor. The test sensor may also be used to determine gas flows, assisting the calibration or supporting the signal analysis of the gas sensor system under normal operation.

Figure 1:
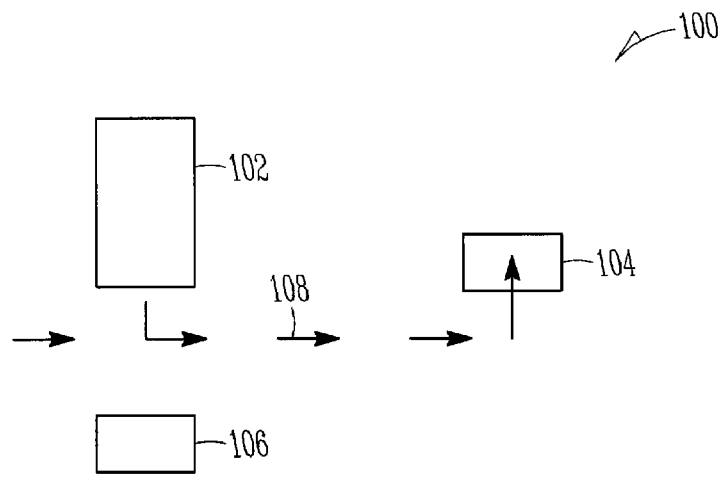
FIG. 1 illustrates a schematic diagram of gas sensor test system, according to some embodiments.
Figure 2:
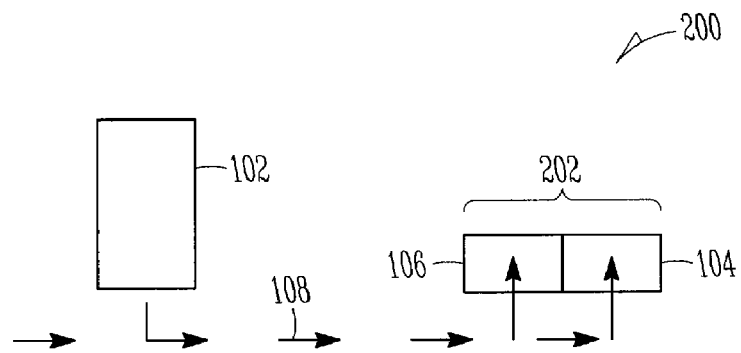
FIG. 2 illustrates a schematic diagram of an alternate configuration of a gas sensor test system, according to some embodiments.

Referring to FIG. 1, a schematic diagram of a gas sensor test system 100 is shown, according to some embodiments. The gas sensor test system 100 includes a gas generating device 102 positioned near a target gas sensor 104, such that a test gas generated may pass 108 to the target gas sensor 104. A test sensor 106 may also be positioned near the gas generating device 102, such that the test gas passes 106 to the test sensor 106. The test sensor 106 may be adjacent to or in contact with the target sensor 104, such that they form an integrated sensor 202 (as illustrated in FIG. 2, for example).

The test sensor 106 may be a physical sensor, such as a thermal conductivity sensor, for example. The test sensor 106 may also include a metal oxide sensor or thin gold film, for example. Using the resistance of a thin gold film may determine the concentration of a test gas, such as hydrogen sulfide, for example. The test sensor 106 may be inexpensive and stable when compared to the target gas sensor 104. A microbridge may be used as a flow sensor and as a thermal conductivity sensor, for example. The microbridge may be integrated within a silicon wafer, for example. The target gas sensor 104 may include a combustible gas sensor, such as a pellistor, for example. The test gas may be a hydrocarbon, for example. Test gases may include hydrogen, methane, propane, butane or pentane, for example.

The gas generating device 102 may include a heater and gas releasing material, such as in commonly owned U.S. patent application Ser. No. 11/618,398 (now U.S. Pat. No. 7,655,186 (Tobias), entitled "GAS GENERATION FOR SENSOR CALIBRATION", filed the same day herewith and incorporated herein in its entirety.

Figure 3:
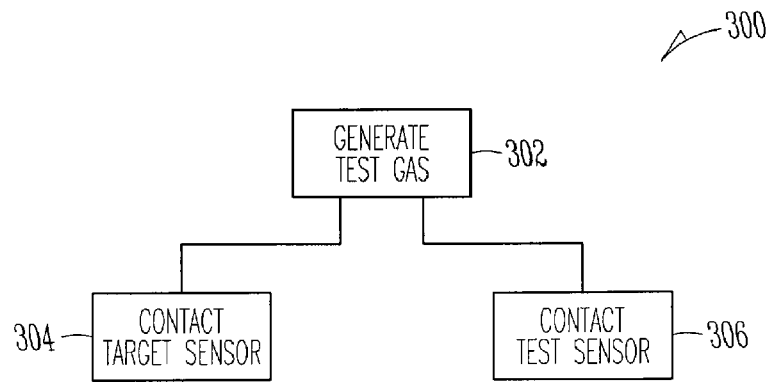
FIG. 3 illustrates a block flow diagram of a method of calibrating a gas sensor, according to some embodiments.

Referring FIG. 3, a block flow diagram of a method 300 of testing a gas sensor is shown, according to some embodiments. A test gas may be generated 302 by a gas generating device, for example. The test gas may contact 304 a target sensor and contact a test sensor 306, simultaneously or in any order, for example.

The test gas may be generated 302 by mixing a gas releasing material or by heating a gas releasing material, for example. Contacting 304, 306 may include exposing the sensors to the test gas by passive diffusion, for example.

The test gas may contact the target sensor and test sensor, sufficient to determine the amount of test gas generated and also to test the target sensor. The test may be a bump test or a calibration test. The bump test exposes a high enough concentration of the test gas to the sensor for the sensor alarm to trigger, effectively testing the functionality of the sensor. A calibration provides a concentration suitable to reset the baseline concentration, effectively correcting for any drift or contamination in the sensor. The calibration or bump test may be activated as often as desired, with the only limitation being the amount of gas releasing material available or any electrical or battery power limitations involved with activating the heater. The tests may be performed every few minutes, hourly, daily, weekly, etc.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

The invention claimed is:

1. A gas sensor system, comprising:
   a test gas generating device, adapted to generate a test gas;
   a target combustible gas sensor, positioned near the test gas generating device; and
   one or more thermal conductivity test gas sensors, positioned near the test gas generating device and in communication with the target gas sensor such that the test gas sensor is operable to calibrate or test the target gas sensor;
   wherein the test gas sensor is sensitive to the test gas;
   wherein the test gas generating device comprises a heater and a test gas releasing material;
   wherein the target combustible gas sensor comprises a pellistor; and
   wherein the test gas comprises a hydrocarbon.

2. The gas sensor system of claim 1, wherein the test gas comprises methane, propane, butane, pentane or a combination thereof.

3. The gas sensor system of claim 1, wherein the test gas comprises methane.

4. A gas sensor system, comprising:
   a test gas generating device, adapted to generate a hydrogen sulfide test gas;
   a target combustible gas sensor comprising a pellistor, positioned near the test gas generating device; and
   a thin gold film test gas sensor, positioned near the test gas generating device and in communication with the pellistor such that the test gas sensor is operable to calibrate or test the target gas sensor;
   wherein the test gas sensor is sensitive to the hydrogen sulfide test gas.

5. A method for testing a gas sensor, the method comprising:
   generating a test gas by heating a test gas releasing material;
   contacting a thermal conductivity test sensor with test gas, sufficient to determine amount of test gas in contact; and
   contacting a target combustible gas sensor with test gas, sufficient to test the target sensor;
   wherein the target combustible gas sensor comprises a pellistor;
   wherein the test gas comprises a hydrocarbon; and
   wherein the test comprises a calibration test or a bump test.

6. A method for testing a gas sensor, the method comprising;
   generating a test gas by mixing a test gas releasing material,
   contacting a thermal conductivity test sensor with the test gas, sufficient to determine amount of test gas in contact; and
   contacting a target combustible sensor with test gas, sufficient to test the target sensor;
   wherein the target combustible gas sensor comprises a pellistor;
   wherein the test gas comprises a hydrocarbon; and
   wherein the test comprises a calibration test or a bump test.

7. A gas sensor system, comprising:
   a test gas generating device, adapted to generate a test gas;
   a target combustible gas sensor, positioned near the test gas generating device; and
   one or more microbridge test gas sensors, positioned near the test gas generating device and in communication with the target gas sensor such that the test gas sensor is operable to calibrate or test the target gas sensor;
   wherein the test gas sensor comprises one or more thermal conductivity test gas sensors sensitive to the test gas;
   wherein the test gas generating device comprises a heater and a test gas releasing material;
   wherein the target combustible gas sensor comprises a pellistor; and
   wherein the test gas comprises a hydrocarbon.

8. The gas sensor system of claim 7, wherein the test gas comprises, methane, propane, butane, pentane or a combination thereof.

9. The gas sensor system of claim 7, wherein the test gas comprises methane.

* * * * *